United States Patent [19]

Mee

[11] 4,202,995
[45] May 13, 1980

[54] PRODUCTION OF GLYCOLS

[75] Inventor: Alec Mee, Middlesbrough, England

[73] Assignee: Imperial Chemical Industries Limited, London, England

[21] Appl. No.: 24,365

[22] Filed: Mar. 27, 1979

[30] Foreign Application Priority Data

Mar. 31, 1978 [GB] United Kingdom ............... 12662/78
Apr. 10, 1978 [GB] United Kingdom ............... 13944/78

[51] Int. Cl.$^2$ ............................................ C07C 29/02
[52] U.S. Cl. .................................................... 568/860
[58] Field of Search ......................................... 568/860

[56] References Cited

U.S. PATENT DOCUMENTS

| | | | |
|---|---|---|---|
| 1,982,545 | 11/1934 | Skarblom | 568/860 |
| 2,071,395 | 2/1937 | Dreyfus | 568/860 |
| 2,780,528 | 2/1957 | Fossan et al. | 568/860 |
| 3,928,474 | 12/1975 | Witheford | 568/860 |
| 4,008,286 | 2/1977 | Hirose et al. | 568/860 |
| 4,045,500 | 8/1977 | Onsager et al. | 568/860 |
| 4,061,868 | 12/1977 | Fumagalli et al. | 568/860 |

Primary Examiner—Joseph E. Evans
Attorney, Agent, or Firm—Cushman, Darby & Cushman

[57] ABSTRACT

A glycol is produced by reacting an olefine with oxygen in an aqueous solution which comprises copper or iron ions, bromide ions, and iodide ions. The catalyst may be recycled to the reaction in the heavy ends of the process.

7 Claims, No Drawings

PRODUCTION OF GLYCOLS

This invention relates to the production of glycols.

It is known to oxidise olefines with oxygen in the presence of aqueous media containing copper or iron bromide from U.S. Pat. No. 4,008,286, which discloses that iodide ions reduce or insolubilise the copper or iron. We have found however that in certain proportions of iodide to bromide ions copper and iron bromides remain acceptably soluble and that improved reaction rates may be obtained.

According to the invention a glycol is produced by contacting an olefine especially ethylene or propylene with oxygen and an aqueous solution which comprises as catalyst copper and/or iron ions, bromide ions and iodide ions, the ratio of iodide ions to bromide ions being in the range 1:1000 to 1:5 and preferably 1:100 to 1:10.

It has been found that the process occurs at attractive rates and good selectivities may also be obtained.

The process may be carried out at a pressure in the range 5–50 bars and preferably 10–30 bars.

The temperature is suitably 100°–225° C. and is preferably 140°–180° C.

The total concentration of copper and iron ions in the solution may be in the range 0.02 to 2 gram atoms per liter and is preferably 0.1 to 1 gram atoms per liter.

The total concentration of iodide and bromide ions is suitably equivalent to the copper and/or iron ions in their highest valency state; however if desired free hydrobromic and/or hydroiodic acid may be present or other anions—for example nitrate or acetate—may be present. It is preferred that the total iodide and bromide ion concentration in the solution should be 0.02 to 2 gram atoms, and preferably 0.1 to 1 gram atoms per liter.

The molar ratio of olefine to oxygen fed to the reaction may be 1:1 to 5:1 and is preferably in the range 2:1 to 3:1. If desired an inert gas for example nitrogen and/or carbon dioxide may be present. It is necessary to avoid flammable conditions in the process.

The process may be carried out in the presence of an additional solvent for example a carboxylic acid having for example 2–6 carbon atoms or a lower alcohol.

A liquid which boils at a higher temperature than the glycol product is preferably present in an amount of 2–80% by weight of the total reaction medium. This allows the glycol product to be distilled from the high boiling liquid whilst catalyst components remain in solution or suspension in the high boiling liquid. This solution or suspension may be recycled to the process. Suitable liquids are higher boiling by-products of the reaction e.g. diethylene glycol, dipropylene glycol, triethylene glycol or tripropylene glycol or lower esters thereof, e.g. the acetates, or other polyol acetates, e.g. triacetin, ethers or inert nitriles e.g. adiponitrile. The higher boiling solvent should form a single phase in the aqueous solution during the production of the glycol. When such a liquid is present any precipitated catalyst components may be removed from the initial reaction product, e.g. by filtering or centrifuging it, and then water preferably together with any dioxan or dimethyl dioxan which may be produced may be distilled in a first distillation, glycol may be distilled from the bottoms product of the first distillation in a second distillation, and a bottoms product from the second distillation (which contains catalyst components) may be recycled to the reaction.

EXAMPLE 1

An aqueous solution (2 liters) containing 0.3 moles/liter of cupric bromide was charged to a 4 liter titanium pressure vessel equipped with stirrer and condenser. The pressure was raised to 200 psig with nitrogen (500 l/h) and the temperature raised to 165° C. Ethylene (120 l/h) and oxygen (50 l/h) were then switched on in addition to the nitrogen. The rate of oxidation was followed by the uptake of oxygen. The residual ethylene and by-product carbon oxides and acetaldehyde were monitored in the exit gas. The build up of intermediates, products and by-products in the liquid phase (e.g. bromohydrin, dibromide, glycol, diglycol, dioxane) was followed by withdrawing small samples at frequent intervals from the reactor.

The rate of oxidation under the above conditions was 3.8 liters/$O_2$/liter/hour and the molar proportion of volatile by products was 13.5%. After 1 hour the free glycol concentration was 1.0% by weight and the molar yield was 68%.

After 1 hour aqueous potassium iodide solution was injected into the reactor to give a concentration of 0.05 moles/liter of iodide. The oxidation rate immediately increased to 15.2 liters $O_2$/liter/hour and then settled out at 9 liters $O_2$/liter/hour while the proportion of volatile by-products fell to 6.5%. After a further 1¾ hours the glycol concentration was 10.8% by weight and the overall yield was 83%.

EXAMPLE 2

An aqueous solution (2 liters) containing 0.3 moles/liter cupric bromide, 0.3 moles/liter ferrous sulphate, 0.72 moles/liter sodium bromide and 0.05 moles/liter hydroiodic acid was charged and reacted as in Example 1 except that the pressure was 300 psig and temperature 160° C. The reaction rate was oxygen limited and the proportion of volatile by-products was 5%. After 2 hours the free glycol concentration was 11.0% by weight and the molar yield has 78%. Much higher free glycol concentrations are possible e.g. 16% by weight but the yield falls rapidly with increasing glycol levels because the further conversion of glycol to dioxane and diglycol becomes progressively more significant e.g. when the free glycol concentration reached 16.5% by weight the molar yield was 66.8%.

EXAMPLE 3

An aqueous solution (2 liters) containing 0.3 moles/liter of copper sulphate and 0.05 moles/liter of potassium iodide was charged and reacted as in Example 1. Negligible oxidation occurred. Sodium bromide 0.6 moles/liter was then added. The oxidation rate settled out at 9 liters $O_2$/liter/hour and the molar proportion of volatile by-products was 6.5%. The concentration of free glycol after 3 hours was 12.9% by weight and the molar yield was 89%.

The injection of a further 0.05 moles/liter potassium iodide produced no additional permanent improvement.

The concentrations of glycol in the above examples were determined by gas/liquid chromatography. The yields are based on the ethylene consumed. The molar proportions of volatile by-products are based on the ethylene consumed.

psig = pounds per square inch gauge

I claim:

1. A process which comprises producing a glycol by contacting an olefin with oxygen and an aqueous solution which comprises as catalyst copper and/or iron ions, bromide ions and iodide ions, the ratio of iodide ions to bromide ions being in the range 1:1000 to 1.5.

2. A process as claimed in claim 1 in which the ratio of iodide ions to bromide ions is 1:100 to 1:10.

3. A process as claimed in claim 1 which is carried out at a pressure in the range 10 to 30 bars.

4. A process as claimed in claim 1 in which the temperature is 140° to 180° C.

5. A process as claimed in claim 1 in which the total concentration of copper and iron ions in the solution is 0.1 to 1 gram atoms per liter and the total iodide and bromide ions concentration is 0.1 to 1 gram atoms per liter.

6. A process as claimed in claim 1 in which the molar ratio of olefin to oxygen fed to the reaction is in the range 2:1 to 3:1.

7. A process as claimed in any preceding claim in which the olefin is ethylene.

* * * * *